United States Patent [19]
Goto et al.

[11] Patent Number: 5,761,953
[45] Date of Patent: Jun. 9, 1998

[54] METHOD OF DETECTING THE EMBRITTLEMENT OF TWO-PHASE STAINLESS STEEL

[75] Inventors: Toru Goto; Takeshi Naito, both of Hyogo-ken; Shintaro Kumano, Tokyo, all of Japan

[73] Assignee: Mitsubishi Jukogyo Kabushiki Kaisha, Tokyo, Japan

[21] Appl. No.: 725,486

[22] Filed: Oct. 4, 1996

[30] Foreign Application Priority Data

Jun. 11, 1996 [JP] Japan .................... 8-149321

[51] Int. Cl.$^6$ .................... G01N 17/00; G01N 33/20; G01N 3/00; G01N 3/40
[52] U.S. Cl. .................................................... 73/86
[58] Field of Search .................... 73/86, 87, 78, 73/82

[56] References Cited

U.S. PATENT DOCUMENTS

| | | | |
|---|---|---|---|
| 4,428,781 | 1/1984 | Norstrom | 148/333 |
| 4,461,168 | 7/1984 | Kobayashi | 73/87 |
| 4,719,583 | 1/1988 | Takafuji et al. | 73/78 X |

FOREIGN PATENT DOCUMENTS

| | | |
|---|---|---|
| 04235347 | 8/1992 | Japan . |
| 2 150 305 | 6/1985 | United Kingdom . |

OTHER PUBLICATIONS

*Modelling of Microstructural Evolution and Mechanical Properties of Steel Plates Produced by Thermo–Mechanical Control Process*, A. Yoshie et al., ISIJ International, vol. 32, No. 3, 1992, pp. 395–404 month not give.

Primary Examiner—Thomas P. Noland
Attorney, Agent, or Firm—Bell Seltzer Intellectual Property Law Group; Alston & Bird LLP

[57] ABSTRACT

The main object of the present invention is to permit the non-destructive examination of the embrittlement of two-phase stainless steel. There remains anxiety about the reliability of methods based on conventional formulae because an actual machine is not examined to confirm its degree of embrittlement, and its Charpy impact absorption energy at room temperature cannot be estimated accurately. The present invention provides a method of detecting the embrittlement of two-phase stainless steel, which comprises measuring the hardness of the ferrite phase and the hardness of austenite phase of two-phase stainless steel along with reading (1) the area ratio of the ferrite phase from microstructure observation, (2) the area ratio of the ferrite phases and the space between the ferrite phases from microstructure observation, or (3) the area ratio of the ferrite phase, the space between the ferrite phases, and the occupying ratio of carbide in the grain boundary length from microstructure observation to estimate the Charpy impact absorption energy at room temperature of the two-phase stainless steel.

1 Claim, 11 Drawing Sheets

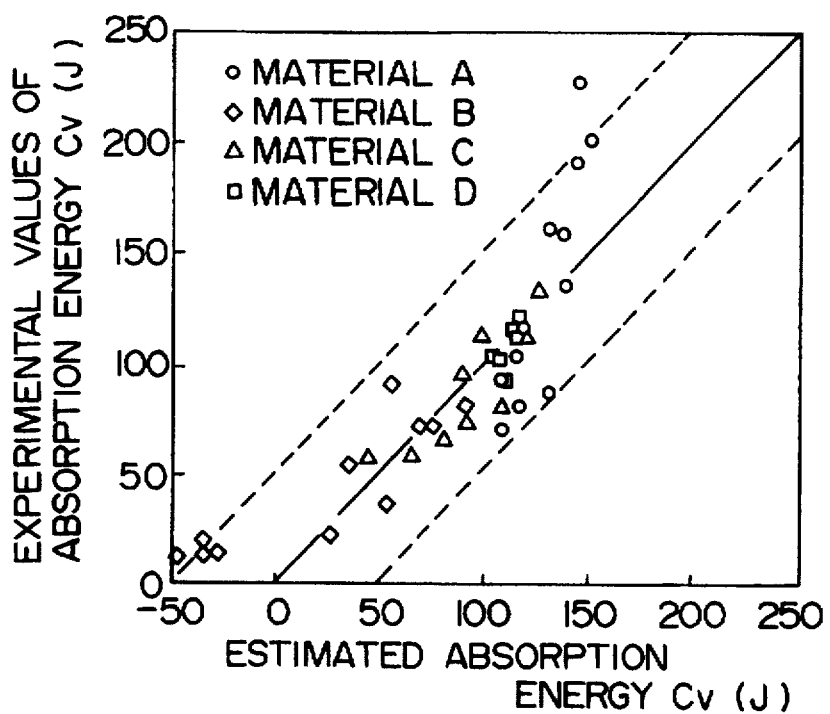
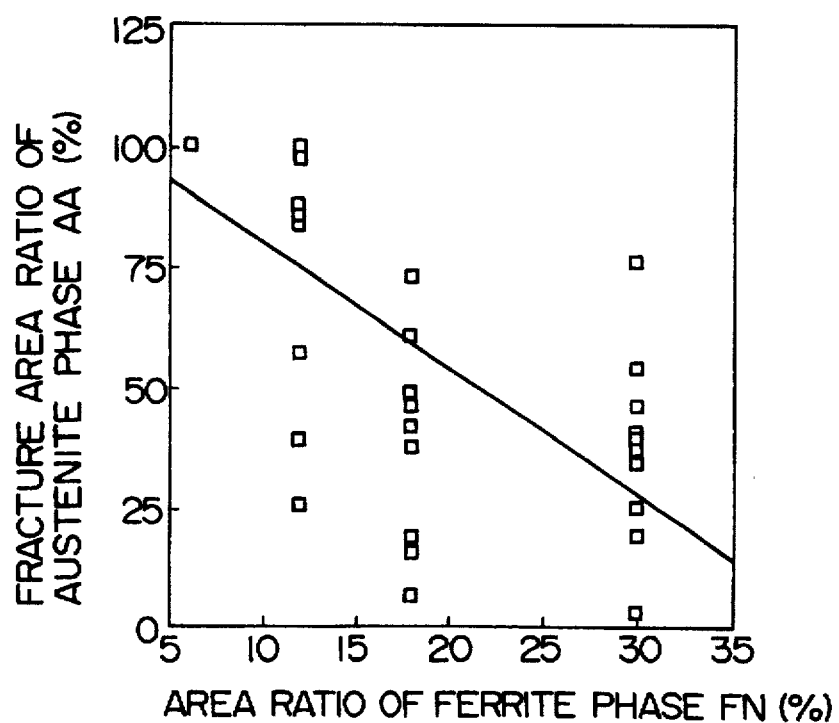

α(FERRITE PHASE)

METHOD OF DETECTING THE EMBRITTLEMENT OF TWO-PHASE STAINLESS STEEL

BACKGROUND OF THE INVENTION

1. Field of the Invention

The present invention relates to a method of detecting the degree of embrittlement of two-phase stainless steel and in particular to a method of detecting the embrittlement, and estimating the degree of embrittlement, of two-phase stainless steel in cooling tubes, pump casings etc. in a pressurized water reactor.

2. Description of the Related Art

For a method of estimating the degree of embrittlement of a member of two-phase stainless steel, there is proposed a formula by which the degree of embrittlement can be estimated from chemical components, operation temperature and operation time. However, there is no method of estimating the degree of embrittlement by examining the state of an actual machine.

There remains anxiety about the reliability of a method based on such formula because an actual machine is not examined to confirm its degree of embrittlement.

SUMMARY OF THE INVENTION

The present invention was made under these circumstances, and the object of the invention is to provide a method of detecting the embrittlement of two-phase stainless steel in which Charpy impact absorption energy can be directly obtained from measurements capable of non-destructive examination, or estimated by examination, based on the mechanism of embrittlement of two-phase stainless steel as well as on the theory of Charpy impact absorption energy of two-phase material.

The first aspect of the present invention relates to a method of detecting the embrittlement of two-phase stainless steel, which comprises measuring the hardness of the ferrite phase ($\alpha$-phase), and the hardness of the austenite phase ($\gamma$-phase) of two-phase stainless steel, along with reading the area ratio of the ferrite phase from microstructure observation to estimate the Charpy impact absorption energy at room temperature of the two-phase stainless steel from the above specified 3 values.

The second aspect of the present invention relates to a method of detecting the embrittlement of two-phase stainless steel, which comprises measuring the hardness of the ferrite phase, and the hardness of the austenite phase of two-phase stainless steel, along with reading the area ratio of the ferrite phase and the space between the ferrite phases from microstructure observation to estimate the Charpy impact absorption energy at room temperature of the two-phase stainless steel from the above specified 4 values.

The third aspect of the present invention relates to a method of detecting the embrittlement of two-phase stainless steel, which comprises measuring the hardness of the ferrite phase, and the hardness of the austenite phase of two-phase stainless steel, along with reading the area ratio of the ferrite phase, the space between the ferrite phases, and the occupying ratio of carbide in the grain boundary length from microstructure observation to estimate the Charpy impact absorption energy at room temperature of the two-phase stainless steel from the above specified 5 values.

DETAILED DESCRIPTION OF THE INVENTION

The first aspect of the present invention is described below in detail.

Measurements capable of non-destructive examination includes hardness of ferrite phase, $H_VF$, hardness of austenite phase, $H_VA$, and area ratio of ferrite phase, FN.

The Charpy impact absorption energy, $C_V$, of two-phase stainless steel may be expressed as follows:

$$C_V = g \times \{(AF/100) \times C_VF + (AA/100) \times C_VA\} \quad \ldots (1)$$

where AF and AA are the area ratios of ferrite and austenite phases respectively on a fracture of a test specimen after testing; g is a coefficient of correction; AF+AA=100; $C_VF$ is the absorption energy of ferrite phase.

In equation (1), AF+AA=100 where $C_VF$ is the absorption energy of ferrite phase; and $C_VA$ is the absorption energy of austenite phase.

To become hard with embrittlement is a general characteristic of a material. Hence, we think that $C_VF$ and $C_VA$ can be estimated from the hardness $H_VF$ and $H_VA$ of the respective phases. It is assumed that they can be expressed in e.g. the following equations (2) and (3):

$$C_VF = bF \times H_VF + aF \quad \ldots (2)$$

$$C_VA = bA \times H_VA + aA \quad \ldots (3)$$

It is further assumed that the area ratio AA of the austenite phase expressed in terms of the area ratio AF of the ferrite phase (or 100-AF) on a fracture can be expressed by the area ratio FN of the ferrite phase. For example, it can be assumed that AA can be expressed by the following equation (4):

$$AA/100 = dF \times FN/100 + cF(=1-AF/100) \quad \ldots (4)$$

If the above assumptions can hold, Charpy impact absorption energy can be estimated from $H_VF$, $H_VA$ and FN by the above equation (1). That is, degree of embrittlement (usually estimated by a decrease in absorption energy etc.) can be estimated by non-destructive examination.

Hence, two-phase stainless steel having various degrees of embrittlement is prepared and determined for Experimental $C_V$ (experimental value of absorption energy), $H_VF$, $H_VA$, AF (AA) and FN, to formulate an optimum estimation equation.

The optimum estimation equation refers to an equation where $I_{error}$ expressed by the following equation (5) reaches minimum:

$$I_{error} = \sum_i (\text{Estimated } C_{vi} - \text{Experimental } C_{vi})^2 \quad (5)$$

where Estimated $C_V$ is estimated absorption energy; Experimental $C_V$ is experimental absorption energy; and i means each test material.

The estimation equation thus obtained is as shown in the following equation (6) where Charpy impact absorption energy is expressed in terms of 3 examinable values, $H_VF$, $H_VA$ and FN.

$$\text{Estimated } C_V = g \times \{dF \times FN/100 + cF)(bA \times H_VA + aA) + (1 - dF \times FN/100 - cF)(bF \times H_VF + aF)\} \quad \ldots (6)$$

where g is a coefficient of correction.

The Charpy impact absorption energy of an actual machine can be obtained from non-destructively examinable and obtainable measurements from the actual machine, i.e. hardness of ferrite phase $H_VF$, hardness of austenite phase $H_VA$, and area ratio of ferrite phase, FN. A decrease in absorption energy indicates embrittlement and can thus serves as an indicator of degree of embrittlement.

According to the first aspect of the present invention, there can be provided a method of detecting the embrittlement of two-phase stainless steel in which Charpy impact absorption energy can be directly obtained from measurements capable of non-destructive examination, or estimated by examination, based on the mechanism of embrittlement of two-phase stainless steel as well as on the theory of Charpy impact absorption energy of two-phase material.

In the first aspect of the present invention, the Charpy impact absorption energy at room temperature of two-phase stainless steel is estimated from 3 values obtained by measuring the hardness of the ferrite phase, $H_VF$, and the hardness of the austenite phase, $H_VA$, of two-phase stainless steel along with reading the area ratio of the ferrite phase from microstructure observation to estimate the embrittlement of of a member of two-phase stainless steel, but there is a scattering of ±70 J. According to the second aspect of the present invention, the improvement of estimation accuracy (±20 J) can be achieved by adding the space between the ferrite phases, FS, as estimation information.

The second aspect of the present invention is a method of detecting the embrittlement of two-phase stainless steel, which comprises measuring the hardness of the ferrite phase and the hardness of the austenite phase of two-phase stainless steel, along with reading the area ratio of the ferrite phase and the space between the ferrite phases from microstructure observation to estimate the Charpy impact absorption energy at room temperature of the two-phase stainless steel from the above specified 4 values.

The second aspect of the present invention is described below in detail.

Measurements capable of non-destructive examination includes hardness of ferrite phase, $H_VF$, hardness of austenite phase, $H_VA$, area ratio of ferrite phase, FN, and space between ferrite phases, FS.

The Charpy impact absorption energy of two-phase stainless steel, $C_V$, may be expressed in the following formula (7) assuming that 100-AA is the area ratio of the ferrite phase, and AA is the area ratio of the austenite phase, on a fracture of a test specimen after testing:

$$C_V = g \times \{(1-AA/100) \times C_VF + (AA/100 \times C_VA)\} \quad \ldots (7)$$

where $C_VF$ is the absorption energy of the ferrite phase; $C_VA$ is the absorption energy of the austenite phase; and g is a coefficient of correction.

To become hard with embrittlement is a general characteristic of a material. Combining this with the fact shown in FIG. 5 that is discussed later, we think that $C_VF$ and $C_VA$ can be estimated from the hardness $H_VF$ and $H_VA$ of the respective phases. It is assumed that they can be expressed in the following equations (8) and (9):

$$C_VF = aF + bF \times H_VF \quad \ldots (8)$$

$$C_VA = aA + bA \times H_VA \quad \ldots (9)$$

where aF, bF, aA and bF are constants.

It is further assumed that the area AA of the austenite phase on a fracture of a test specimen after testing can be expressed in terms of the area ratio FN, or 1-FN, of the ferrite phase on microstructure by e.g. the following equation (10):

$$1 - AA/100 = cF + dF \times FN/100 \quad \ldots (10)$$

where cF and dF are constants.

If the above assumptions can hold, Charpy impact absorption energy at room temperature can be estimated from $H_VF$, $H_VA$ and FN. That is, degree of embrittlement (usually estimated by a decrease in absorption energy etc.) can be estimated by non-destructive examination.

However, the space between the ferrite phases may not be identical even if the ferrite phase is present in the same amount of FN as microstructure. The space between the ferrite phases, FS, are automatically determined in 3 divided lines at the X-axis side and 4 divided lines at the Y-axis side in an image-processing unit by incorporation of a few microphotographs. FS is expressed by the following equation (11):

$$FS = \sum_{i=1}^{n} Li/n \quad (11)$$

where Li is the space between the ferrite phases in measurement lines, and n is the number of times of measurements.

At present, there is no theoretical ground of how FS functions in response to an impact value.

Hence, two-phase stainless steels having various degrees of embrittlement are prepared and determined for Experimental $C_V$ (experimental value of absorption energy), $H_VF$, $H_VA$, FN and FS, to formulate an optimum estimation equation.

The optimum estimation equation refers to an equation where $I_{error}$ expressed by the following equation (5) reaches minimum:

$$I_{error} = \sum_i (\text{Estimated } C_{vi} - \text{Experimental } C_{vi})^2 \quad (5)$$

where Estimated $C_V$ is estimated absorption energy; Experimental $C_V$ is experimental absorption energy; and i means each test material.

The estimation equation thus obtained is as shown in the following equation (12) where Charpy impact absorption energy can be expressed in terms of 4 examinable values, $H_VF$, $H_VA$, FN and SN:

$$\text{Estimated } C_V = g \times (1 + eF \times FS + hF \times FS^2) \{(1-dF \times FN/100-cF) (bA \times H_VA + aA) + (dF \times FN/100 + cF) (bF \times H_VF + aF)\} \quad \ldots (12)$$

where g is a coefficient of correction; and eF, hF, dF, cF, bA, aA, dF, bF, and aF are constants.

If the respective constants are determined in estimation equation (12), the Charpy impact absorption energy of an actual machine can be obtained from non-destructively examinable and obtainable measurements from the actual machine, i.e. hardness of ferrite phase, $H_VF$, hardness of austenite phase $H_VA$, area ratio of ferrite phase, FN, and space between ferrite phases FS. A decrease in absorption energy indicates embrittlement and can thus serves as an indicator of degree of embrittlement.

According to the second aspect of the present invention, there can be provided a method of detecting the embrittlement of two-phase stainless steel in which Charpy impact absorption energy can be directly obtained from measurements capable of non-destructive examination, or estimated by examination, based on the mechanism of embrittlement of two-phase stainless steel as well as on the theory of Charpy impact absorption energy of two-phase material.

However, estimate accuracy worsened with a correlation coefficient of 0.876 as shown in FIG. 7, when Charpy impact absorption energy at room temperature is estimated non-destructively by the above formula (12) from hardness of ferrite phase, hardness of austenite phase, area ratio of ferrite phase, and space between ferrite phases using steel materials heated for 10,000 hours as input data besides the above-mentioned data, on the basis of the mechanism of embrittlement of two-phase stainless steel and the theory of Charpy impact absorption energy of two-phase material.

This worsening is probably due to the fact that a part of the steel materials heated for a long time at high temperature initiated to undergo significant grain boundary release on its fracture after impact testing. This grain boundary release is the phenomenon in which α- and γ-phases are separated from each other along a brittle grain boundary having much precipitated carbide upon application of outer strength (arrows) on the interface therebetween (see FIG. 8). Because said grain boundary release results from the precipitation of carbide, the measurement of occupying ratio of carbide in grain boundary length is added as one parameter to permit further accurate estimation of Charpy impact absorption energy at room temperature to solve said problem.

The third aspect of the present invention is made under these circumstances and the object is to provide a method of detecting the embrittlement of two-phase stainless steel, wherein Charpy impact absorption energy at room temperature can be estimated with higher accuracy from the hardness of the ferrite phase, the hardness of the austenite phase, the area ratio of the ferrite phase, the space between the ferrite phases, and the occupying ratio of carbide in grain boundary length, in two-phase stainless steel.

In the third aspect of the present invention, the area ratio of the ferrite phase is determined in the following manner. Assuming that the ferrite phase (α-phase) is interspersed as shown in FIG. 9, the area ratio of the α-phase, FN (%), is as follows:

$$FN = l(sum\ of\ ferrite\ phase\ areas/total\ area) \times 100 \quad \ldots (13)$$

In the third aspect of the present invention, the space between the ferrite phases is determined by the equation (14). That is, in FIG. 10, the distance between ferrite island-shaped phases adjacent to each other is measured in 4 lines parallel to the Y axis and 3 lines parallel to the X axis to determine FS in the following equation (14):

$$FS = \sum_{i=1}^{n} Li/n \quad \ldots (14)$$

where the distance between ferrite phases is FS, the distance between a ferrite phase and another ferrite phase is Li, and the affix i is the number of times of measurements.

In the third aspect of the present invention, the above occupying ratio of carbide in grain boundary length is determined in the following manner. Assuming that carbide (arrows) is interspersed as shown in FIG. 11, the occupying ratio (%) of carbide in grain boundary length is determined by the following equation (15). In FIG. 11, grain boundary is indicated as the line of grain boundary.

$$LC = (L_C/L_A) \times 100 \quad \ldots (15)$$

where LC is the occupying ratio (%) of carbide in grain boundary length; $L_C$ is total length of carbide; and $L_A$ is the sum of grain boundary length.

Hereinafter, the third aspect of the present invention is described in detail.

Estimate accuracy worsened with a correlation coefficient of 0.876 when Charpy impact absorption energy at room temperature was estimated in a non-destructive manner by the previous estimation equation (the above equation (12) using steel materials heated at a high temperature for a long time (10,000 hours) in addition to a conventional data base (up to 3000 hours).

Hence, a fracture (i.e. a face appearing on destruction by testing) of the steel heated for a long time was examined, and it was found that the grain boundary, where ferrite phase/austenite phases were separated from each other, tended to show more fracture than conventional one. Further examination of this boundary under a transmission-type electron microscope indicated that precipitated carbide is larger than in conventional one.

We estimated that the Charpy impact absorption energy at room temperature of two-phase stainless steel is expressed by the following equation (16):

$$C_V = g \times \{C_V F \times AF/100 + C_V A \times AA/100 + C_V R \times AS/100\} \quad \ldots (16)$$

where AF and AA are the area ratios of ferrite and austenite phases respectively on a fracture of a test specimen after testing; AS is the area ratio of the released grain boundary; AF+AA+AS=100%; $C_V F$ is the absorption energy of the ferrite phase; $C_V A$ is the absorption energy of the austenite phase; and $C_V R$ is the absorption energy of the released grain boundary. The area ratio of released grain boundary AS (%) is a value obtained by dividing the sum of grain boundary areas on a fracture by the total area and it is determined by the following equation (17):

$$AS = (sum\ of\ grain\ boundary\ areas\ on\ fracture)/(total\ area) \times 100 \quad \ldots (17)$$

Now, the non-destructive handling with AS and $C_V R$ is described.

$C_V = AFC_V F + AAC_V A$ appearing on the equation (16) corresponds to a fundamental equation of the equation (12), and $ASC_V R$ adopted newly in the estimation equation is described as follows:

The relationship among the fracture ratio of released grain boundary AS observed on a fracture after testing, the occupying ratio of carbide in grain boundary measured by observation of the microstructure (the same meaning as "occupying ratio of carbide in grain boundary length" in the claims), and LC, is shown by plots in FIG. 12. In FIG. 12, the relationship between LC and AS is expressed as a straight line passing the common origin of materials A3, A4, and B2, but this relationship was previously formulated such that the straight line passes the origin, and usually k0 ranges from the+side to the−side. In addition, there is a material dependence between LC and AS, but there is a good correspondence between AS and LC. With respect to the material dependence, it was found that the area ratio of ferrite phase FN shows a good correspondence to the slope β of the straight line expressing the relationship of AS-LS. The relationship between AS and LC is shown in the following equation:

$$AS = k0 + \beta LC \quad \ldots (18)$$

The relationship between the slope β of the straight line and the area ratio of ferrite FN is shown in the following equation:

$$\beta = C0 + C1 \times FN \quad \ldots (19)$$

Hence, the area ratio of released grain boundary, AS, can be expressed by combination of the above equations (18) and (19), as follows:

$$AS=\{k0+(C0+C1 \times FN) \times LC\} \quad \ldots (20)$$

The non-destructive estimation of the absorption energy of released grain boundary interface, $C_VR$, is not feasible and is shown as a material constant because none is correlated with $C_VR$ as a state of grain boundary, although other absorption energies such as $C_VF$ (the absorption energy of the ferrite phase) and $C_VA$ (the absorption energy of the austenite phase) can be correlated with $H_VF$ (the hardness of the ferrite phase) and $H_VA$ (the hardness of the austenite phase) as shown in the relationships $C_VF=aF+bF \times H_VF$ and $C_VA=aA+bA \times H_VA$ respectively.

If the foregoing can hold, Charpy impact absorption energy can be estimated from $H_VF$, $H_VA$, FN, FS, and LC by use of the above formula (16). In the following equation (21), Charpy impact absorption energy is expressed in terms of 5 examinable values, $H_VF$, $H_VA$, FN, FS, and, LC:

$$\text{Estimated } C_V = g \times (1+eF \times FS + hF \times FS^2) \{(1-dF \times FN/100-ef)(bA \times H_VA + aA) + (dF \times FN/100 + cF)(bF \times H_VF + aF)\} + \{(C0+C1 \times FN) \times LC + k0\}/100 \times C_VR \quad \ldots (21)$$

where g is a coefficient of correction; eF, hF, dF, eF, bA, aA, bF, aF, C0, C1, and k0 are constants; and $C_VR$ is a material constant.

The estimation equation (the above equation (21)) can be used for determination of Charpy impact absorption energy from measurements i.e. hardness of ferrite phase, $H_VF$, hardness of austenite phase, $H_VA$, area ratio of ferrite phase, FN, space between ferrite phases, FS, and occupying ratio of carbide, LC, all of which can be obtained by non-destructive examination of an actual machine. A decrease in absorption energy indicates embrittlement and can thus serves as an indicator of degree of embrittlement.

When $C_V$ was estimated from the above equation (21), the correlation coefficient was 0.896, indicating higher accuracy than in the equation (12).

According to the third aspect of the present invention, there can be provided a method of detecting the embrittlement of two-phase stainless steel capable of estimating Charpy impact absorption energy at room temperature with high accuracy from hardness of ferrite phase, hardness of austenite phase, area ratio of ferrite phase, space between ferrite phases, and occupying ratio of carbide in grain boundary length, of two-phase stainless steel.

BRIEF DESCRIPTION OF THE DRAWINGS

FIG. 1 is a characteristic drawing showing the effect of the estimation of impact absorption energy according to one example of the first aspect of the present invention.

FIG. 2 is a characteristic drawing showing the relationship between the area ratio of the fractured austenite phase and the area ratio of the ferrite phases.

DETAILED DESCRIPTION OF PREFERRED EMBODIMENTS

The first aspect of the present invention is described with reference to the following example.

Example 1

4 kinds of two-phase stainless steel (A to D) were prepared and heated at 350° C., 400° C., and 450° C. for a long time (up to 3000 hours). The area ratio of the ferrite phase (not changed by heating) was 12% in material A, 30% in material B, 18% in material C, and 6.2% in material D. The hardness of the austenite phase scarcely changed, and Vickers hardness determined with 25 g loading before heating was 206 for material A, 212 for material B, 247 for material C, and 252 for material D.

Table 1 shows Charpy absorption energy Experimental $C_V$ at room temperature, Vickers hardness of the ferrite phase (1 g loading), $H_VF$, and the area ratio AA (%) of the austenite phase obtained from fracture, of heated materials A to D (partially containing materials before heating).

TABLE 1

| Materials | Heating Temp. (°C.) | Heating Hour (h) | Experimental $C_V$ (J) | $H_VF$ | AA (%) |
|---|---|---|---|---|---|
| A | 350 | 1000 | 201 | 381 | 88 |
|   |     | 3000 | 159 | 439 | 85 |
|   | 400 | 300  | 192 | 409 | 100 |
|   |     | 1000 | 136 | 436 | 88 |
|   |     | 3000 | 105 | 540 | 84 |
|   | 450 | 300  | 227 | 409 | 100 |
|   |     | 1000 | 161 | 468 | 98 |
|   |     | 3000 | 94  | 566 | 84 |
| B | 350 | 300  | 82  | 379 | 40 |
|   |     | 1000 | 73  | 402 | 76 |
|   |     | 3000 | 92  | 434 | 25 |
|   | 400 | 300  | 73  | 412 | 39 |
|   |     | 1000 | 37  | 437 | 54 |
|   |     | 3000 | 21  | 573 | 37 |
|   | 450 | 1000 | 55  | 465 | 46 |
|   |     | 3000 | 15  | 564 | 19 |
| C | —   | 0    | 135 | 303 | 42 |
|   | 350 | 300  | 114 | 314 | 46 |
|   |     | 1000 | 82  | 354 | 16 |
|   |     | 3000 | 73  | 448 | 40 |
|   | 400 | 300  | 97  | 404 | 49 |
|   |     | 1000 | 67  | 429 | 61 |

TABLE 1-continued

| Materials | Heating Temp. (°C.) | Heating Hour (h) | Experimental $C_v$ (J) | $H_vF$ | AA (%) |
|---|---|---|---|---|---|
| | | 3000 | 60 | 472 | 19 |
| | 450 | 300 | 116 | 376 | 73 |
| | | 1000 | 75 | 399 | 16 |
| | | 3000 | 59 | 527 | 7 |
| D | — | 0 | 118 | 308 | 100 |
| | 350 | 300 | 116 | 328 | 100 |
| | | 1000 | 114 | 353 | 100 |
| | | 3000 | 116 | 369 | 100 |
| | 400 | 300 | 116 | 359 | 100 |
| | | 1000 | 94 | 383 | 100 |
| | | 3000 | 105 | 479 | 100 |
| | 450 | 300 | 122 | 331 | 100 |
| | | 1000 | 117 | 370 | 100 |
| | | 3000 | 103 | 439 | 100 |

Figure 4:
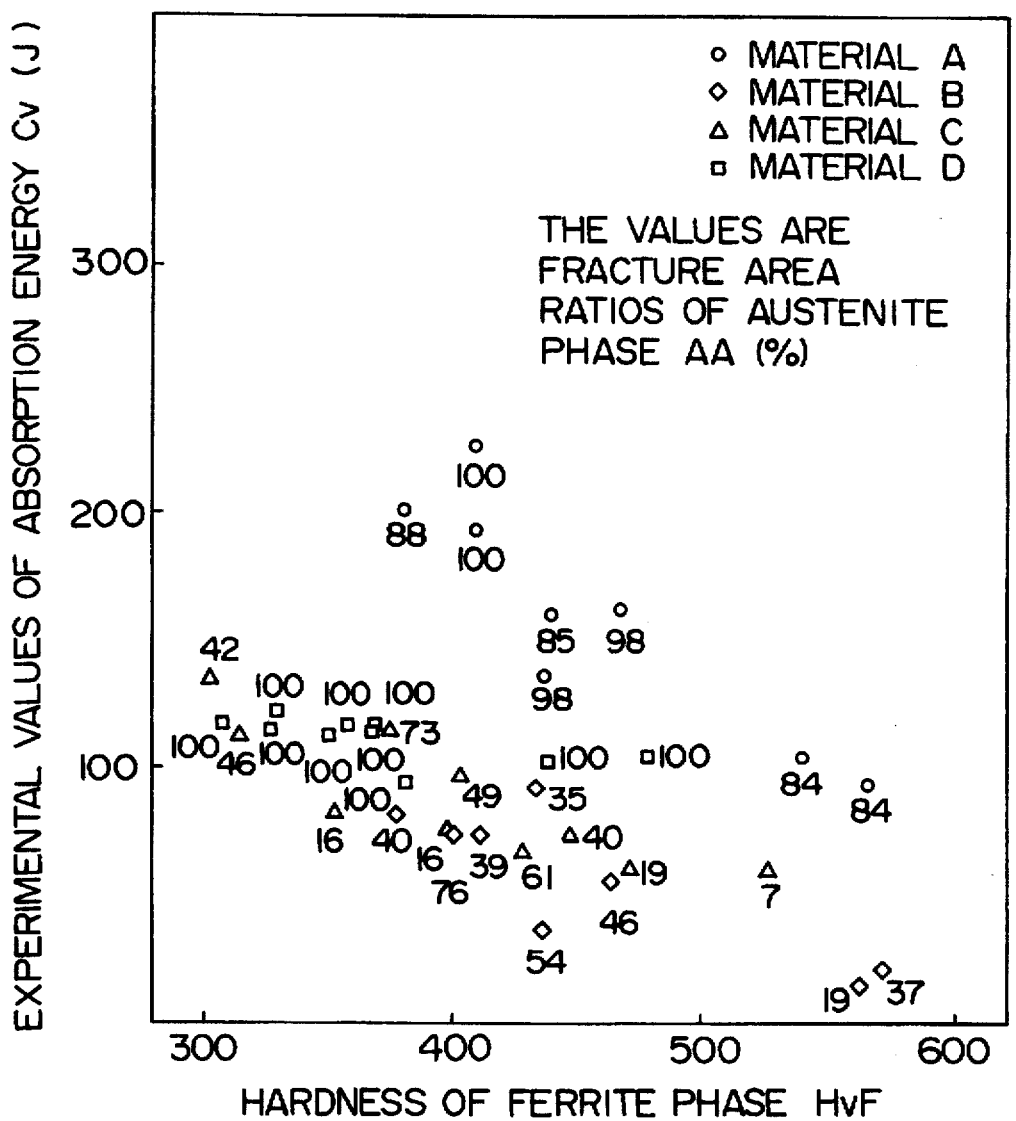
FIG. 4 is a characteristic drawing showing experimentally determined impact absorption energy at room temperature, the hardness of the ferrite phase and the fracture ratio of the austenite phase.

FIG. 4 shows the relationship between Experimental $C_V$ and $H_vF$. FIG. 4 shows that Charpy absorption energy of each material tends to decrease with increasing hardness of the ferrite phase. This indicates the propriety of proposed equations (2) and (3).

First, it was examined whether the equation (1) can hold or not. The equation was corrected as follows:

$$\text{Estimated } C_V = g \times \{AA/100 \, (bA \, H_vA + aA) + (1-AA/100)(bF \, H_vF + aF)\} \quad \ldots (22)$$

where g is a coefficient of correction.

Figure 3:
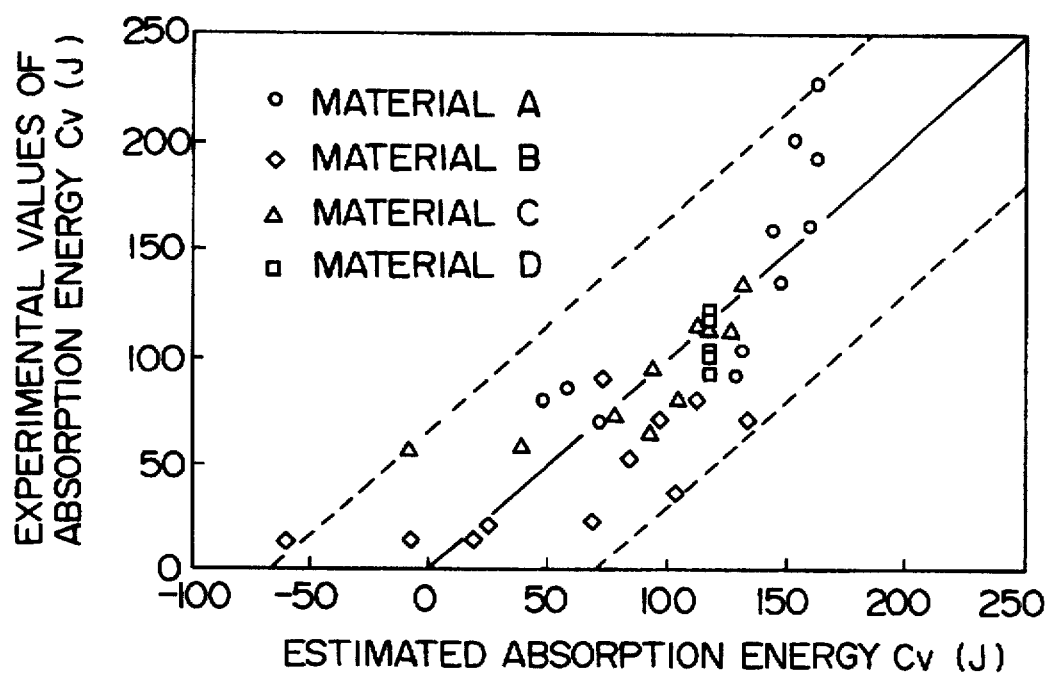
FIG. 3 is a characteristic drawing showing the result of the estimation of impact absorption energy from the hardness of each phase and the fracture ratio of the austenite phase.

The relationship between absorption energy (Estimated $C_V$) which could be estimated from the results obtained using experimental data and the experimental results (Estimated $C_V$) is shown in FIG. 3. Although there is a scattering of ±70 J therebetween, there is the 1:1 relationship. The scattering of ±70 J is considered practically small enough to estimate absorption energy, indicating that the equation (1) is appropriate.

As a result of examination of the method of estimating the fracture ratio of austenite (AA), it was found that as shown in FIG. 2, there is a correlation between AA and area ratio of ferrite phase (FN) with a correlation coefficient of 0.721 in the primary equation. The relationship was able to be expressed in the following equation (23):

$$AA/100 = -2.628 \, FN/100 + 1.07 \quad \ldots (23)$$

Then, the equation (23) is combined with the equation (22) to obtain the optimum estimation equation (6) by which absorption energy (Estimated $C_V$) was estimated. The relationship between absorption energy (Estimated $C_V$) and experimental value (Experimental $C_V$) is shown in FIG. 1 to provide estimation with approximately the same accuracy as in FIG. 3. The respective constants in equation (6) are: g=0.21, bA=−6.5, aA=2200 J, bF=−4.2, aF=1900 J, dF=−2.628, and cF=1.07. In FIG. 1, AA=−2.628× FN+106.67 (%).

Hence, the absorption energy at room temperature of an actual machine can be estimated from the equation (6) using hardness and area ratio determined for the ferrite phase and hardness determined for austenite phase of the actual machine.

According to the above example, the mechanism of embrittlement of two-phase stainless steel results from the decomposition of the ferrite phase into Cr-rich phase and Fe-rich phase by spinodal decomposition etc., and the ferrite phase of two-phase stainless steel is hardened with proceeding embrittlement. Because the austenite phase does not change at the temperature at which two-phase stainless steel is usually used, it is generally considered that its absorption energy becomes smaller as it becomes hardened. We, could arrive at the equation for estimating Charpy impact absorption energy by using measurements (hardness of ferrite phase, hardness of austenite phase, and area ratio of ferrite phase) examinable on an actual machine, from the foregoing idea and the simple assumption that the impact absorption energy of a material with two different phases is the sum of values obtained by multiplying the impact absorption energy of each single phase by its corresponding fracture area. This permits the non-destructive examination of the degree of embrittlement of an actual machine.

Then, the second aspect of the present invention is described with reference to the following example.

Example 2

4 kinds of two-phase stainless steel (A1, A2, B1, and C1) were prepared and heated at 350° C., 400° C., and 450° C. for a long time (up to 3000 hours). The area ratio of the ferrite phase (not changed by heating) was 12% in material A1, 30% in material A2, 18% in material B1, and 6.2% in material C1. The hardness of the austenite phase scarcely changed, and Vickers hardness determined with 25 g loading before heating was 163 for material A1, 184 for material A2, 179 for material B1, and 190 for material C1.

Tables 2 to 5 show the hardness of the ferrite phase (1. g loading), $H_vF$, the hardness of the austenite phase (25 g loading), $H_vA$, and Charpy absorption energy, Experimental $C_V$, the area ratio of the ferrite phase, FN, and the space between the ferrite phases, FS, obtained from the microstructure, of the respective heated materials A1, A2, B1, and C1 (partially containing materials before heating).

TABLE 2

| (Material A1) | | | | | | | | | Image analysis | |
|---|---|---|---|---|---|---|---|---|---|---|
| Nominal ferrite amount (FN) | Heating temp. (°C.) | Heating hours (hr) | $H_vF$ $H_v(0.001)$ | $H_vA$ $H_v(0.025)$ | $C_v$(J) | Fracture ratio (%) | | | Ferrite area ratio FN (%) | Ferrite spaces FS (μm) |
| | | | | | | Ductility (D) | Cleavage (B) | Interphase separation | | |
| 12 | No heating | 0 | 307 | 163 | 269 | 100 | 0 | 0 | 10.3 | 78.9 |
| | 350 | 300 | 363 | 157 | 209 | 100 | 0 | 0 | 11.4 | 62.0 |
| | | 1000 | 381 | 170 | 201 | 88 | 11 | 1 | 11.6 | 84.6 |
| | | 3000 | 439 | 162 | 159 | 85 | 13 | 2 | 9.7 | 78.9 |
| | | 10000 | — | — | 88 | 26 | 64 | 10 | — | — |

TABLE 2-continued (Material A1)

| Nominal ferrite amount (FN) | Heating temp. (°C.) | Heating hours (hr) | $H_vF$ $H_v(0.001)$ | $H_vA$ $H_v(0.025)$ | $C_v(J)$ | Fracture ratio (%) Ductility (D) | Cleavage (B) | Interphase separation | Image analysis Ferrite area ratio FN (%) | Ferrite spaces FS (μm) |
|---|---|---|---|---|---|---|---|---|---|---|
| | 400 | 300 | 409 | 156 | 192 | 100 | 0 | 0 | 11.4 | 70.5 |
| | | 1000 | 436 | 165 | 136 | 88 | 10 | 2 | 9.2 | 83.6 |
| | | 3000 | 540 | 161 | 105 | 84 | 14 | 2 | 11.2 | 56.2 |
| | | 10000 | — | — | 82 | 39 | 61 | 0.2 | — | — |
| | 450 | 10 | 409 | 152 | 227 | 100 | 0 | 0 | 12.1 | 71.1 |
| | | 100 | 468 | 159 | 161 | 98 | 2 | 0 | 12.3 | 73.1 |
| | | 3000 | 566 | 169 | 94 | 84 | 11 | 5 | 10.6 | 59.3 |
| | | 10000 | — | — | 72 | 57 | 34 | 8 | — | — |

$C_v(J)$: Experimental $C_v$(absorption energy at room temperature)
Interphase separation: interphase separation (S), separated areas present in the boundary between α- and γ-phases.

TABLE 3

(Material A2)

| Nominal ferrite amount (FN) | Heating temp. (°C.) | Heating hours (hr) | $H_vF$ $H_v(0.001)$ | $H_vA$ $H_v(0.025)$ | $C_v(J)$ | Fracture ratio (%) Ductility (D) | Cleavage (B) | Interphase separation | Image analysis Ferrite area ratio FN (%) | Ferrite spaces FS (μm) |
|---|---|---|---|---|---|---|---|---|---|---|
| 30 | No heating | 0 | 319 | 184 | 300 | 100 | 0 | 0 | 25.1 | 44.4 |
| | 350 | 300 | 379 | 186 | 82 | 40 | 60 | 0 | 25.2 | 45.0 |
| | | 1000 | 402 | 181 | 73 | 76 | 23 | 1 | 20.9 | 43.6 |
| | | 3000 | 434 | 180 | 92 | 25 | 72 | 3 | 26.8 | 44.5 |
| | | 10000 | — | — | 23 | 39 | 53 | 8 | — | — |
| | 400 | 300 | 412 | 182 | 73 | 39 | 59 | 2 | 24.8 | 50.7 |
| | | 1000 | 437 | 182 | 37 | 54 | 46 | 0 | 25.3 | 30.0 |
| | | 3000 | 573 | 182 | 21 | 37 | 59 | 4 | 18.9 | 46.4 |
| | | 10000 | — | — | 15 | 34 | 50 | 16 | — | — |
| | 450 | 10 | 375 | 182 | 262 | 100 | 0 | 0 | 29.3 | 44.1 |
| | | 100 | 465 | 179 | 55 | 46 | 51 | 3 | 27.5 | 45.4 |
| | | 3000 | 564 | 182 | 15 | 19 | 73 | 8 | 15.9 | 46.8 |
| | | 10000 | — | — | 13 | 3 | 71 | 26 | — | — |

$C_v(J)$: Experimental $C_v$(absorption energy at room temperature)
Interphase separation: interphase separation (S), separated areas present in the boundary between α- and γ-phases.

TABLE 4

(Material B1)

| Nominal ferrite amount (FN) | Heating temp. (°C.) | Heating hours (hr) | $H_vF$ $H_v(0.001)$ | $H_vA$ $H_v(0.025)$ | $C_v(J)$ | Fracture ratio (%) Ductility (D) | Cleavage (B) | Interphase separation | Image analysis Ferrite area ratio FN (%) | Ferrite spaces FS (μm) |
|---|---|---|---|---|---|---|---|---|---|---|
| 18 | No heating | 0 | 303 | 179 | 135 | 42 | 42 | 6 | 16.8 | 53.0 |
| | 350 | 300 | 314 | 190 | 114 | 46 | 48 | 2 | 19.7 | 38.4 |
| | | 1000 | 354 | 163 | 82 | 16 | 70 | 8 | 21.1 | 59.2 |
| | | 3000 | 448 | 181 | 73 | 40 | 51 | 4 | 18.0 | 58.8 |
| | 400 | 300 | 404 | 167 | 97 | 49 | 44 | 3 | 18.9 | 51.8 |
| | | 1000 | 429 | 174 | 67 | 61 | 35 | 1 | 17.3 | 63.0 |
| | | 3000 | 472 | 174 | 60 | 19 | 58 | 8 | 16.7 | 53.9 |
| | 450 | 10 | 376 | 171 | 116 | 73 | 24 | 1 | 16.6 | 84.8 |
| | | 100 | 399 | 178 | 75 | 16 | 83 | 1 | 13.9 | 66.8 |
| | | 3000 | 527 | 173 | 59 | 7 | 91 | 2 | 18.2 | 64.5 |

$C_v(J)$: Experimental $C_v$(absorption energy at room temperature)
Interphase separation: interphase separation (S), separated areas present in the boundary between α- and γ-phases.

TABLE 5

(Material C1)

| Nominal ferrite amount (FN) | Heating temp. (°C.) | Heating hours (hr) | $H_vF$ $H_v(0.001)$ | $H_vA$ $H_v(0.025)$ | $C_v(J)$ | Fracture ratio (%) | | | Image analysis | |
|---|---|---|---|---|---|---|---|---|---|---|
| | | | | | | Ductility (D) | Cleavage (B) | Interphase separation | Ferrite area ratio FN (%) | Ferrite spaces FS (μm) |
| 6.2 | No heating | 0 | 308 | 190 | 118 | 100 | 0 | 0 | 9.6 | 40.4 |
| | 350 | 300 | 328 | 186 | 116 | 100 | 0 | 0 | 7.5 | 35.5 |
| | | 1000 | 353 | 203 | 114 | 100 | 0 | 0 | 8.8 | 52.6 |
| | | 3000 | 369 | 172 | 116 | 100 | 0 | 0 | 11.7 | 32.4 |
| | 400 | 300 | 359 | 187 | 116 | 100 | 0 | 0 | 7.7 | 51.5 |
| | | 1000 | 383 | 206 | 94 | 100 | 0 | 0 | 6.3 | 54.5 |
| | | 3000 | 479 | 200 | 105 | 100 | 0 | 0 | 8.8 | 39.6 |
| | 450 | 10 | 331 | 169 | 122 | 100 | 0 | 0 | 7.9 | 49.1 |
| | | 100 | 370 | 176 | 117 | 100 | 0 | 0 | 3.9 | 61.0 |
| | | 3000 | 439 | 195 | 103 | 100 | 0 | 0 | 9.0 | 37.8 |

$C_v(J)$: Experimental $C_v$(absorption energy at room temperature)
Interphase separation: interphase separation (S), separated areas present in the boundary between α- and γ-phases.

Figure 5:
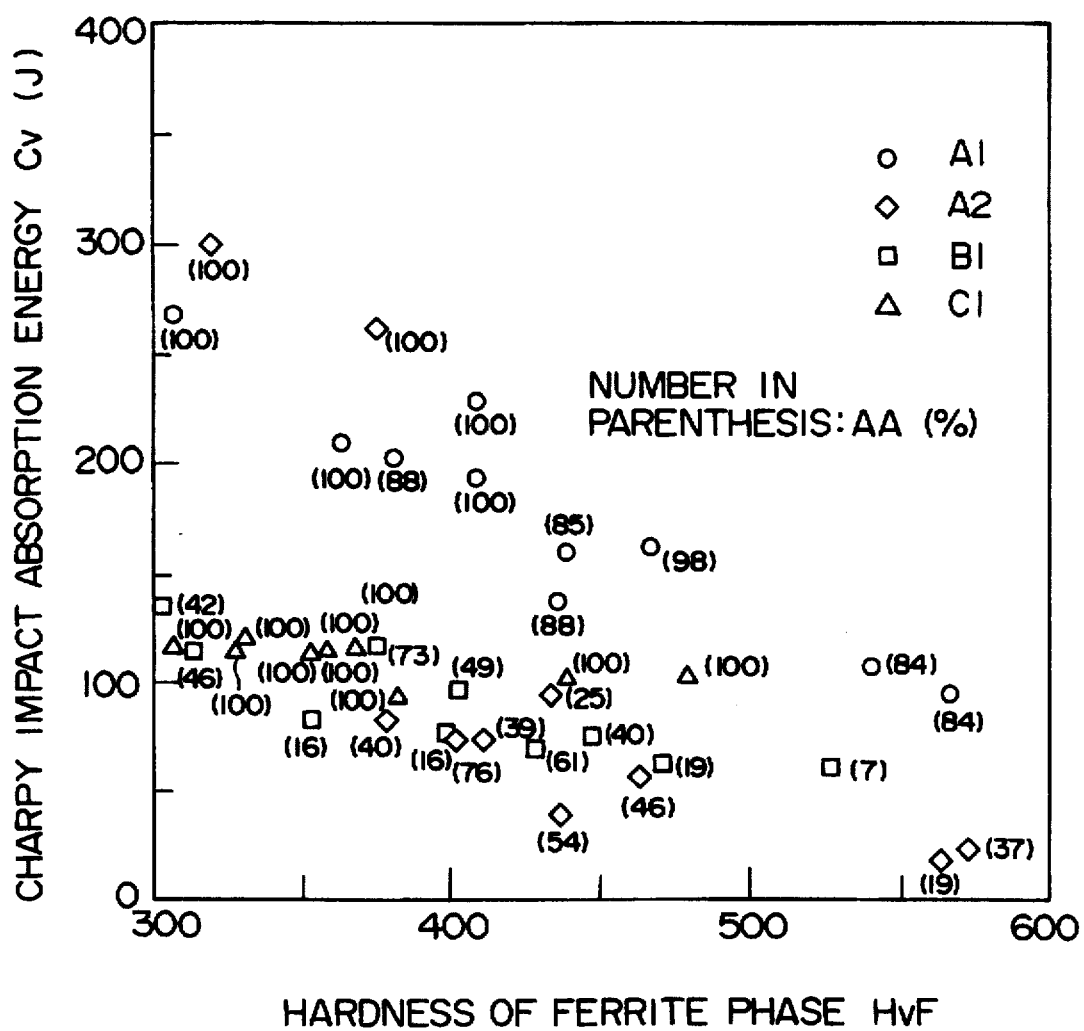
FIG. 5 is a characteristic drawing showing the relationship among experimentally determined impact absorption energy at room temperature, the hardness of the ferrite phase and the fracture ratio of the austenite phase.

FIG. 5 shows the relationship between Experimental $C_v$ and $H_vF$. As can be seen from FIG. 5, the Charpy absorption energy of each material tends to decrease with increasing hardness of the ferrite phase. This indicates the propriety of proposed equations (8) and (9).

Figure 6:
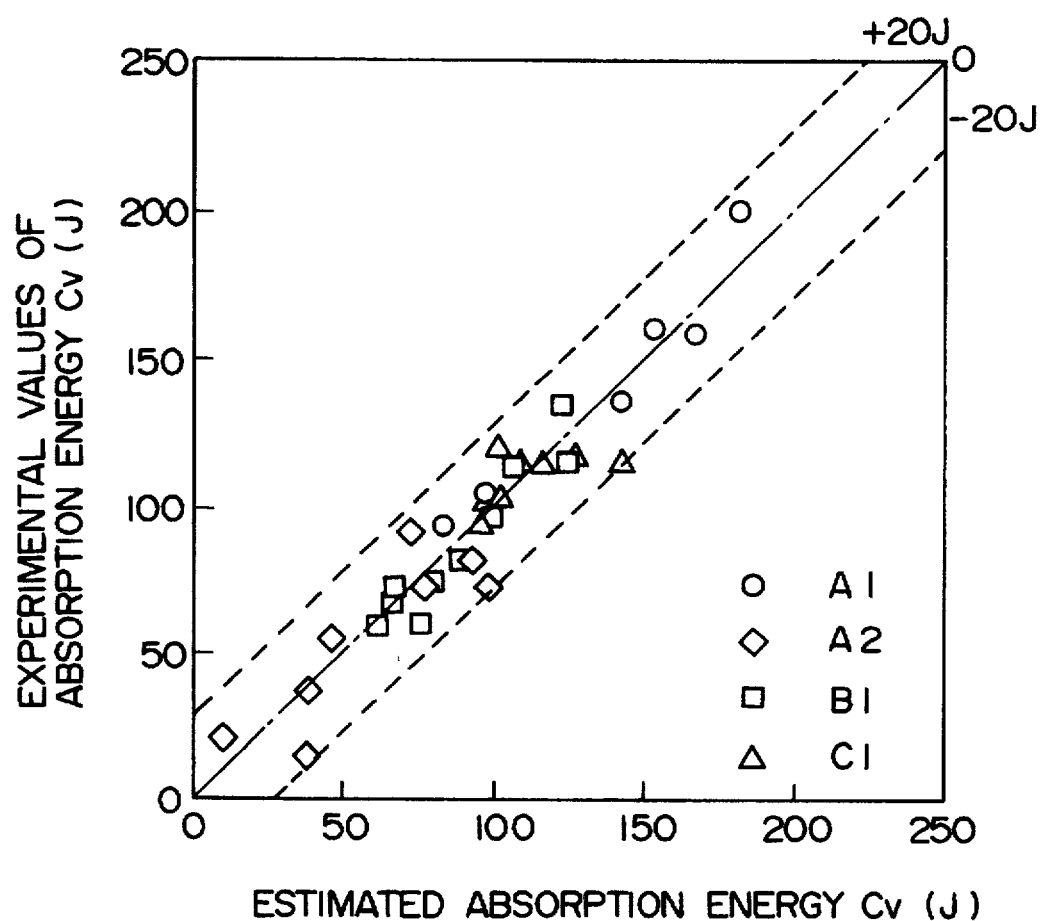
FIG. 6 is a characteristic drawing showing the effect of the method of estimating impact absorption energy according to one example of the second aspect of the present invention

Then, the relationship between absorption energy (Estimated $C_v$) which could be estimated by equation (12) from the experimental data and the experimental results (Estimated $C_v$) is shown in FIG. 6. Although there is a scattering of ±20 J therebetween, there is the 1:1 relationship. The scattering of ±70 J according to the 1st aspect of this invention could be improved to the scattering of ±20 J by addition of a factor of space between ferrite phases.

The scattering of ±20 J is considered practically small to estimate absorption energy. Hence, the absorption energy at room temperature of an actual machine can be estimated by equation (12) on the basis of measurements of the hardness of the ferrite phase, the hardness of the austenite phase, the area ratio of the ferrite phase, and the space between the ferrite phases, of the actual machine.

According to the above example, the mechanism of embrittlement of two-phase stainless steel results from the decomposition of the ferrite phase into Cr-rich phase and Fe-rich phase by spinodal decomposition etc., and the ferrite phase of two-phase stainless steel is hardened with proceeding embrittlement. Because the austenite phase does not change at the temperature at which two-phase stainless steel is usually used, it is generally considered that its absorption energy becomes smaller as it becomes hardened. We could arrive at the equation for estimating Charpy impact absorption energy by using measurements (hardness of ferrite phase, hardness of austenite phase, area ratio of ferrite phase, and space between ferrite phases) examinable on an actual machine, from the foregoing idea and the simple assumption that the impact absorption energy of a material with two different phases is the sum of values obtained by multiplying the impact absorption energy of each single phase by its corresponding area ratio. This permits the non-destructive examination of the degree of embrittlement of an actual machine.

The third aspect of the present invention is described with reference to the following example.

Example 3

4 kinds of two-phase stainless steel (A3, A4, B2, and C2) shown below in Tables 6 to 9 were prepared and heated at; 350° C., 400° C., and 450° C. for a long time (up to 10,000 hours). In addition to the 4 kinds of materials, Tables 6 to 9 show ferrite amount % (FN), heating temperature (°C.), heating time (hr), ferrite strength ($H_vF$, Hv (0.001)), austenite hardness ($H_vA$, Hv (0.025)), room temperature absorption energy (Experimental $C_v$) (J), fracture ratio % (ductility, AA; brittleness, AF; release grain boundary, AS), image analysis (ferrite area ratio FN (%)), ferrite space FS % (μ), and carbide occupying ratio LC (%)).

The ferrite amount (not changed by heating) was 10% in material A3, 25% in material A4, 18% in material B2, and 6.6% in material C2. The "ferrite amount" has a wider meaning and is considered to be scattered because the area ratio of the ferrite phase was image-processed with about 100× magnification photograph (5 to 6 areas). The hardness of the austenite phase scarcely changed, and Vickers hardness determined with 25 g loading before heating was 163 for material A3, 184 for material A4, 179 for material B2, and 190 for material C2.

Tables 6 to 9 show the hardness of the ferrite phase (1 g loading), $H_vF$, the hardness of the austenite phase (25 g loading), $H_vA$, and Charpy absorption energy, Experimental $C_v$, the area ratio of the ferrite phase, FN, the space between the ferrites phases, FS, and the occupying ratio of carbide, LC, obtained from the microstructure. The test specimens were of the heated materials A3, A4, B2, and C2 (partially containing materials before heating).

TABLE 6

| Material | Nominal ferrite amount % (FN) | Heating temp. (°C.) | Heating hour (hr) | Ferrite phase hardness $H_vF$ $H_v(0.001)$ | Austenite phase hardness $H_vA$ $H_v(0.025)$ | Room temp. absorption energy Experimental $C_v(J)$ | Fracture ratio (%) Ductility (AA) | Fracture ratio (%) Brittle-ness (AF) | Release grain boundary (AS) | Image analysis Ferrite area ratio FN (%) | Image analysis Ferrite spaces FS (μm) | Carbide occupying ratio LC (%) |
|---|---|---|---|---|---|---|---|---|---|---|---|---|
| A3 | 10 | No heating | 0 | 307 | 163 | 269 | 100 | 0 | 0 | 10.3 | 78.9 | 2 |
|  |  | 350 | 1000 | 381 | 170 | 201 | 88 | 11 | 1 | 11.6 | 84.6 | 19 |
|  |  |  | 3000 | 439 | 162 | 159 | 85 | 13 | 2 | 9.7 | 78.9 | 37 |
|  |  |  | 10000 | 385 | 152 | 88 | 52 | 34 | 15 | 11.6 | 66.5 | 48 |
|  |  | 400 | 1000 | 436 | 165 | 136 | 88 | 10 | 2 | 9.2 | 83.6 | 35 |
|  |  |  | 3000 | 540 | 161 | 105 | 84 | 14 | 2 | 11.2 | 56.2 | 20 |
|  |  |  | 10000 | 439 | 176 | 82 | 39 | 61 | 0.2 | 13.5 | 61.9 | 44 |
|  |  | 450 | 1000 | 468 | 159 | 161 | 98 | 2 | 0 | 12.3 | 73.1 | 26 |
|  |  |  | 3000 | 566 | 169 | 94 | 84 | 11 | 5 | 10.6 | 59.3 | 29 |
|  |  |  | 10000 | 459 | 159 | 72 | 37 | 60 | 3 | 11.4 | 68.2 | 23 |

TABLE 7

| Material | Nominal ferrite amount % (FN) | Heating temp. (°C.) | Heating hour (hr) | Ferrite phase hardness $H_vF$ $H_v(0.001)$ | Austenite phase hardness $H_vA$ $H_v(0.025)$ | Room temp. absorption energy Experimental $C_v(J)$ | Fracture ratio (%) Ductility (AA) | Fracture ratio (%) Brittle-ness (AF) | Release grain boundary (AS) | Image analysis Ferrite area ratio FN (%) | Image analysis Ferrite spaces FS (μm) | Carbide occupying ratio LC (%) |
|---|---|---|---|---|---|---|---|---|---|---|---|---|
| A4 | 25 | No heating | 0 | 319 | 184 | 300 | 100 | 0 | 0 | 25.1 | 44.4 | 2 |
|  |  | 350 | 300 | 379 | 186 | 82 | 40 | 60 | 0 | 25.2 | 45.0 | 2 |
|  |  |  | 1000 | 402 | 181 | 73 | 76 | 23 | 1 | 20.9 | 43.6 | 1 |
|  |  |  | 3000 | 434 | 180 | 92 | 25 | 72 | 3 | 26.8 | 44.5 | 1 |
|  |  |  | 10000 | 390 | 217 | 23 | 9 | 90 | 1 | 26.6 | 38.6 | 1 |
|  |  | 400 | 300 | 412 | 182 | 73 | 39 | 59 | 2 | 24.6 | 50.7 | 3 |
|  |  |  | 1000 | 437 | 182 | 37 | 54 | 46 | 0 | 25.3 | 30.0 | 1 |
|  |  |  | 3000 | 573 | 182 | 21 | 37 | 59 | 4 | 18.9 | 46.4 | 1 |
|  |  |  | 10000 | 476 | 213 | 15 | 7 | 91 | 2 | 23.0 | 54.5 | 5 |
|  |  | 450 | 100 | 465 | 179 | 55 | 46 | 51 | 3 | 27.5 | 45.4 | 7 |
|  |  |  | 3000 | 564 | 182 | 15 | 19 | 73 | 8 | 15.9 | 46.8 | 12 |
|  |  |  | 10000 | 505 | 177 | 13 | 3 | 84 | 13 | 22.9 | 49.4 | 5 |

TABLE 8

| Material | Nominal ferrite amount % (FN) | Heating temp. (°C.) | Heating hour (hr) | Ferrite phase hardness $H_vF$ $H_v(0.001)$ | Austenite phase hardness $H_vA$ $H_v(0.025)$ | Room temp. absorption energy Experimental $C_v(J)$ | Fracture ratio (%) Ductility (AA) | Fracture ratio (%) Brittle-ness (AF) | Release grain boundary (AS) | Image analysis Ferrite area ratio FN (%) | Image analysis Ferrite spaces FS (μm) | Carbide occupying ratio LC (%) |
|---|---|---|---|---|---|---|---|---|---|---|---|---|
| B2 | 18 | No heating | 0 | 303 | 179 | 135 | 42 | 42 | 6 | 16.8 | 53.0 | 15 |
|  |  | 350 | 300 | 314 | 190 | 114 | 46 | 48 | 2 | 19.7 | 38.4 | 4 |
|  |  |  | 1000 | 354 | 163 | 82 | 16 | 70 | 8 | 21.1 | 59.2 | 14 |
|  |  |  | 3000 | 448 | 181 | 73 | 40 | 51 | 4 | 18.0 | 58.8 | 9 |
|  |  |  | 10000 | 351 | 166 | 55 | 5 | 94 | 1 | 18.3 | 62.7 | 4 |
|  |  | 400 | 300 | 404 | 167 | 97 | 49 | 44 | 3 | 18.9 | 51.8 | 16 |
|  |  |  | 1000 | 429 | 174 | 67 | 61 | 35 | 1 | 17.3 | 63.0 | 18 |
|  |  |  | 3000 | 472 | 174 | 60 | 19 | 68 | 8 | 16.7 | 53.9 | 10 |
|  |  |  | 10000 | 420 | 180 | 38 | 18 | 78 | 4 | 16.9 | 74.6 | 20 |
|  |  | 450 | 10 | 376 | 171 | 116 | 73 | 24 | 1 | 16.6 | 84.8 | 24 |
|  |  |  | 100 | 399 | 178 | 75 | 16 | 83 | 1 | 13.9 | 66.8 | 23 |
|  |  |  | 3000 | 527 | 173 | 59 | 7 | 91 | 2 | 18.2 | 64.5 | 20 |
|  |  |  | 10000 | 440 | 176 | 37 | 10 | 88 | 2 | 16.2 | 75.6 | 23 |

TABLE 9

| Material | Nominal ferrite amount % (FN) | Heating temp. (°C.) | Heating hour (hr) | Ferrite phase hardness $H_vF$ $H_v(0.001)$ | Austenite phase hardness $H_vA$ $H_v(0.025)$ | Room temp. absorption energy Experimental $C_v(J)$ | Fracture ratio (%) Ductility (AA) | Fracture ratio (%) Brittleness (AF) | Fracture ratio (%) Release grain boundary (AS) | Image analysis Ferrite area ratio FN (%) | Image analysis Ferrite spaces FS (μm) | Image analysis Carbide occupying ratio LC (%) |
|---|---|---|---|---|---|---|---|---|---|---|---|---|
| C2 | 6.6 | No heating | 0 | 308 | 190 | 118 | 100 | 0 | 0 | 9.6 | 40.4 | 0 |
|  |  | 350 | 300 | 328 | 186 | 116 | 100 | 0 | 0 | 7.5 | 35.5 | 0 |
|  |  |  | 1000 | 353 | 203 | 114 | 100 | 0 | 0 | 6.8 | 52.6 | 0 |
|  |  |  | 3000 | 369 | 172 | 116 | 100 | 0 | 0 | 11.7 | 32.4 | 0 |
|  |  |  | 10000 | 377 | 216 | 96 | 78 | 21 | 1 | 6.4 | 15.2 | 0 |
|  |  | 400 | 300 | 359 | 187 | 116 | 100 | 0 | 0 | 7.7 | 51.5 | 0 |
|  |  |  | 1000 | 383 | 206 | 94 | 100 | 0 | 0 | 6.3 | 54.5 | 0 |
|  |  |  | 3000 | 479 | 200 | 105 | 100 | 0 | 0 | 8.8 | 39.6 | 0 |
|  |  |  | 10000 | 424 | 215 | 100 | 88 | 11 | 1 | 7.3 | 15.1 | 0 |
|  |  | 450 | 10 | 331 | 169 | 122 | 100 | 0 | 0 | 7.9 | 49.1 | 0 |
|  |  |  | 100 | 370 | 176 | 117 | 100 | 0 | 0 | 3.9 | 61.0 | 0 |
|  |  |  | 3000 | 439 | 195 | 103 | 100 | 0 | 0 | 9.0 | 37.8 | 0 |
|  |  |  | 10000 | 448 | 201 | 96 | 39 | 58 | 3 | 6.0 | 18.1 | 0 |

Figure 13:
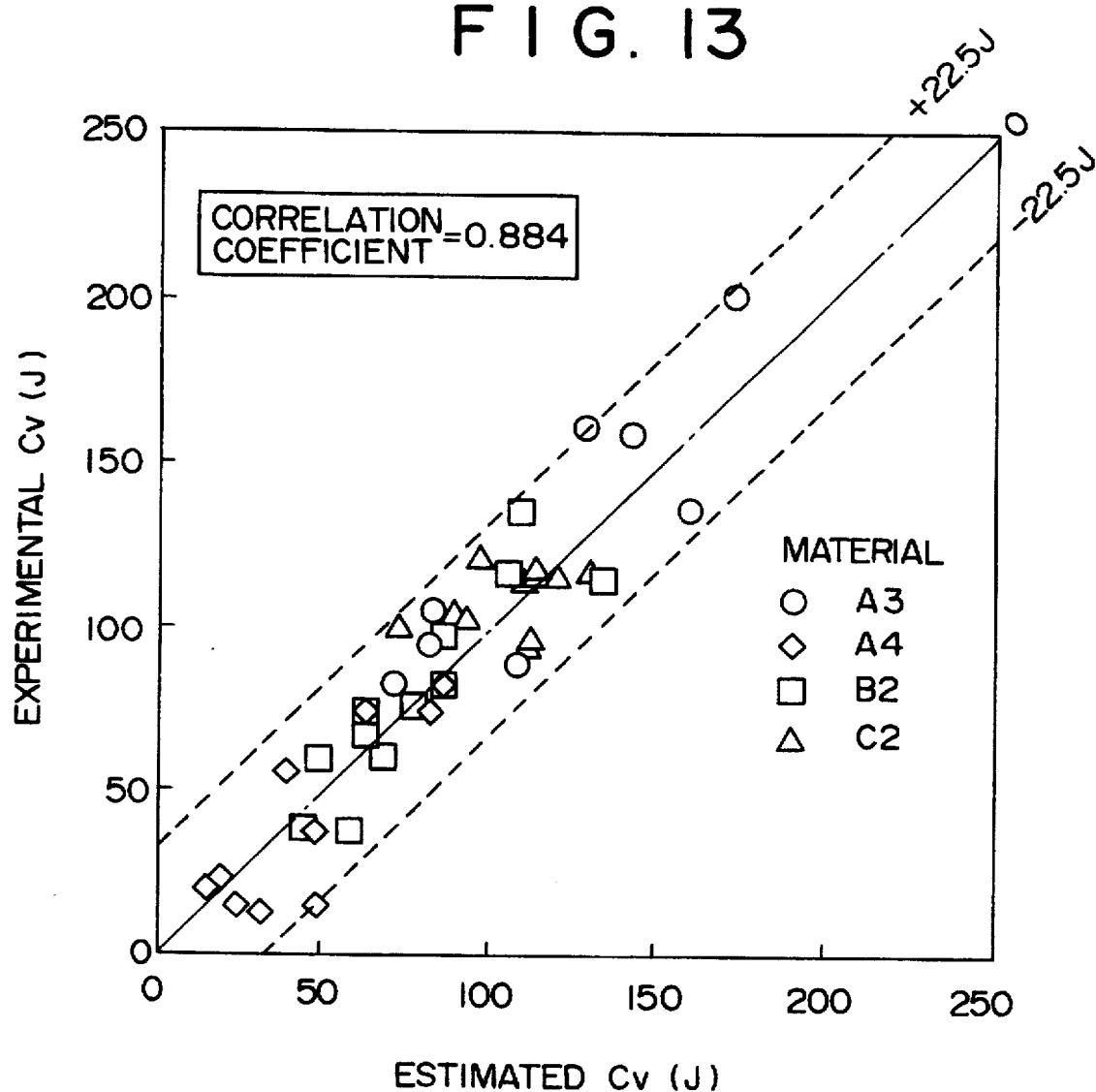
FIG. 13 is a characteristic drawing showing the effect of the method of estimating impact absorption energy according to one example of the third aspect of the present invention.

A correlation coefficient of 0.884 as shown in FIG. 13 is obtained by plotting the relationship between the Charpy absorption energy (Experimental $C_v$) and the estimated absorption energy (Estimated $C_v$) from the above equation (21) using the above values. The coefficient of correction and the constants in equation (21) were calculated using a method known to the art.

The effect according to the above example is as follows:

The correlation of room temperature Charpy impact absorption energy $C_v$ (0.876) from the estimation equation (12), i.e. Estimated $C_v$=g×(1+ef×FS+hF×PS$^2$) {(1-dF×FN/100-ef) (bA×H$_v$A+aA)+(df×FN/100+ef) (bF×H$_v$F+aF)}, worsened using data on the materials heated for a long time (10,000 hours) in addition to the previous data base (up to 3000 hours). Hence, we examined the above estimation equation (16) i.e. $C_v$=g×{AF/100×C$_v$F+AA/100×C$_v$A+AS/100×C$_v$R}.

AS can be expressed in terms of FN and LC in the above formula (20), i.e. AS={k0+ (C0+C1×FN)×LC}, so that the above formula (21), i.e. Estimated $C_v$=g×(1+eF×FS+hf×FS$^2$) {(1-dF×FN/100-eF) (bA×H$_v$A+aA)+(dF×FN/100+eF) (bF×H$_v$F+aF)}+{k0+(C0+C1×FN)×LC}×C$_v$R was obtained to give a good correlation of 0.884 than in the previous estimation equation (12).

Figure 7:
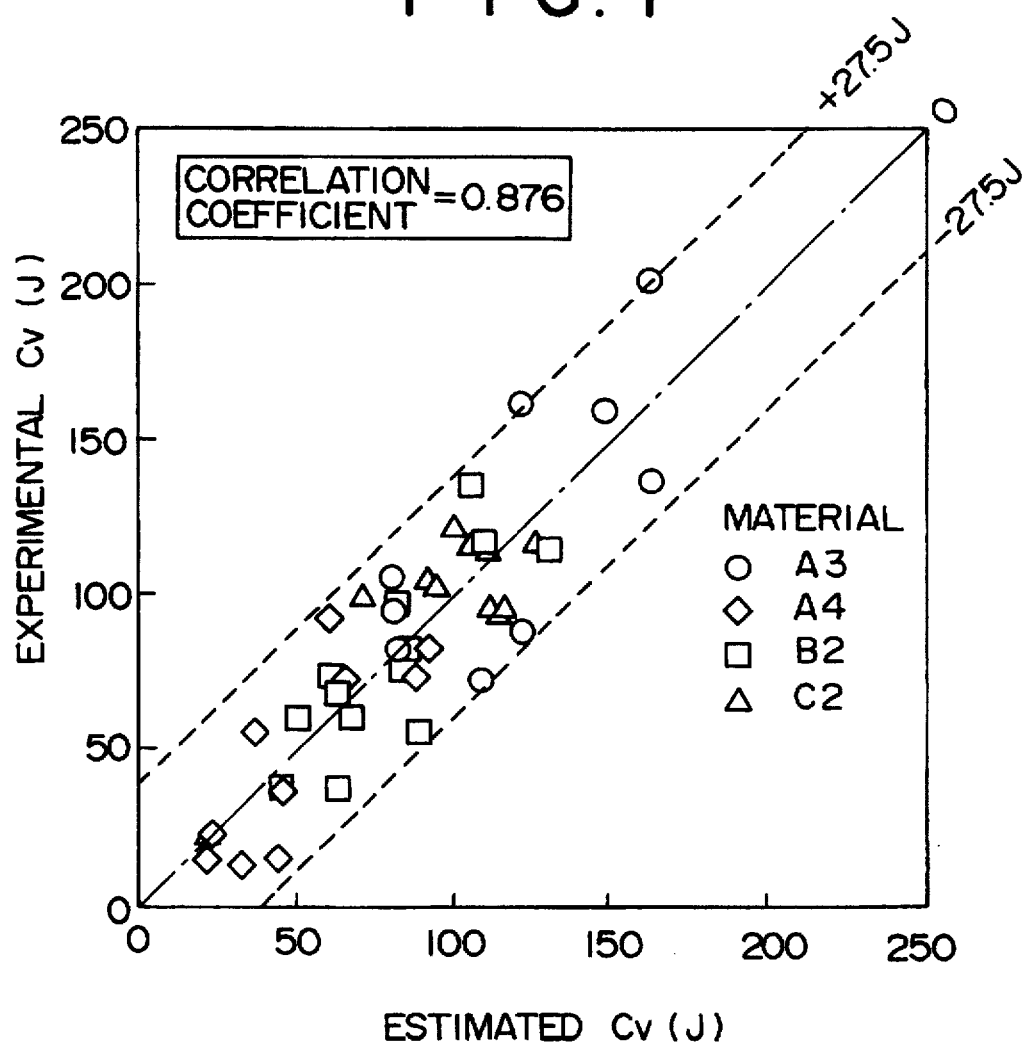
FIG. 7 is a characteristic drawing showing the effect of estimating impact absorption energy based on the equation (12).
Figure 8:
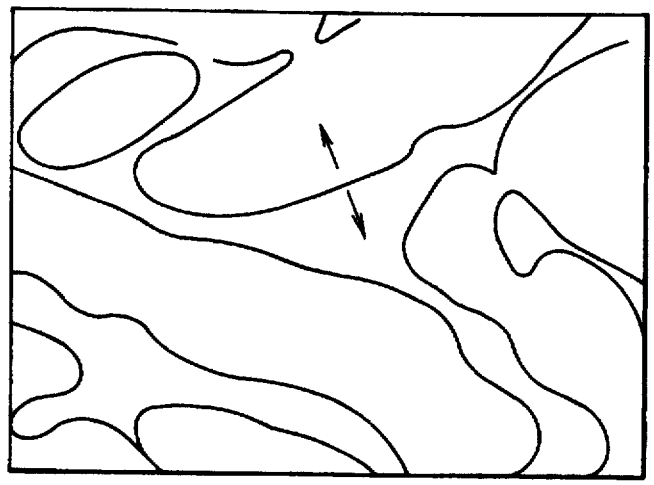
FIG. 8 is a drawing for explaining grain boundary release.
Figure 9:
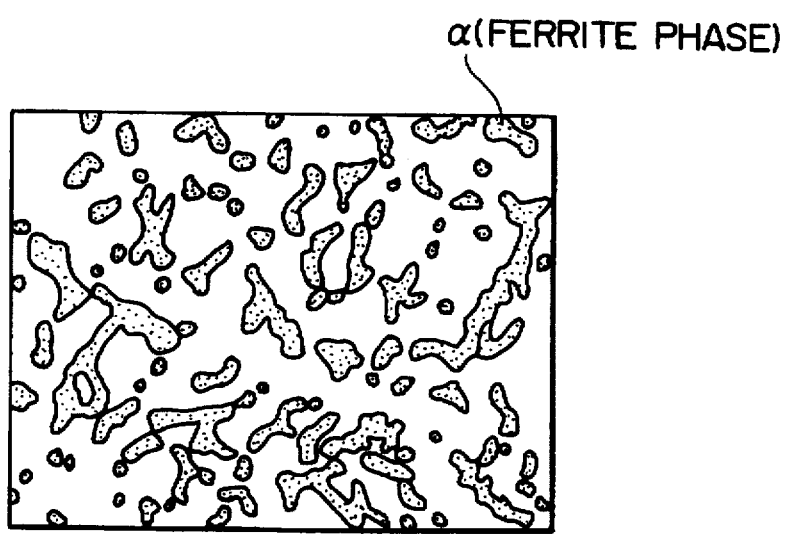
FIG. 9 is a drawing for explaining the determination of the area ratio of the ferrite phase ($\alpha$-phase).
Figure 10:
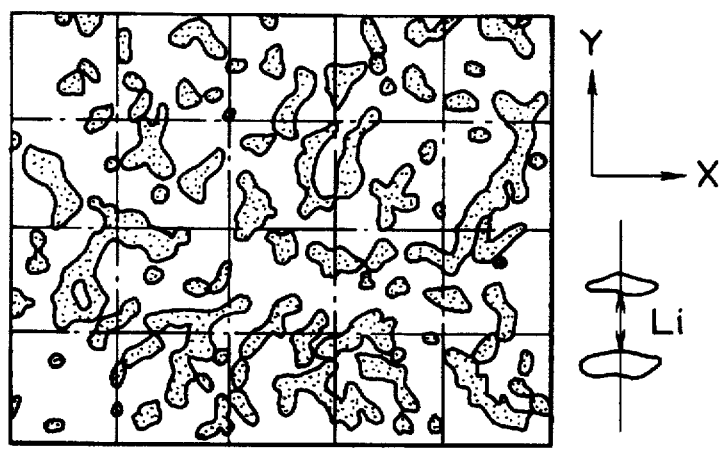
FIG. 10 is a drawing for the determination of the space between the $\alpha$-phases.
Figure 11:
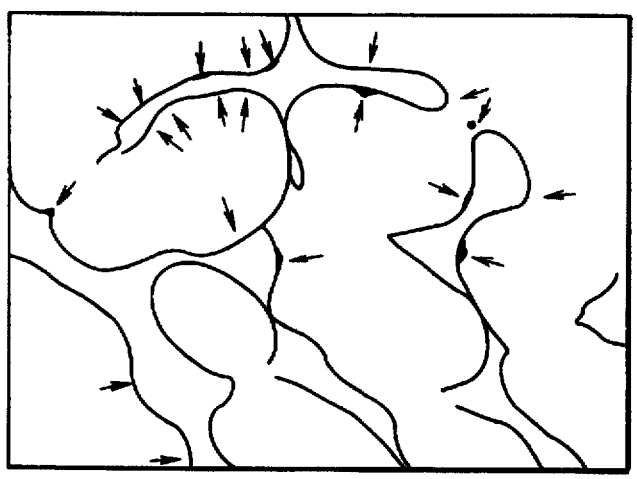
FIG. 11 is a drawing for explaining the occupying ratio of carbide in grain boundary length.

The relationship between the absorption energy (Estimated $C_v$) which could be estimated from the experimental data and the experimental results (Experimental $C_v$) is shown in Table 13. Although there is a scattering of ±22.5 J therebetween, there is the 1:1 relationship. As compared with the scattering of ±27.5 J as shown in FIG. 7 according to the previous equation (12), the scattering of ±22.5 J is practically small to estimate absorption energy. Hence, the absorption energy at room temperature of an actual machine can be estimated by equation (21) on the basis of measurements of the hardness of the ferrite phase, the hardness of the austenite phase, the area ratio of the ferrite phase, the spaces between the ferrite phases, and the occupying ratio of carbide, of the actual machine.

Figure 12:
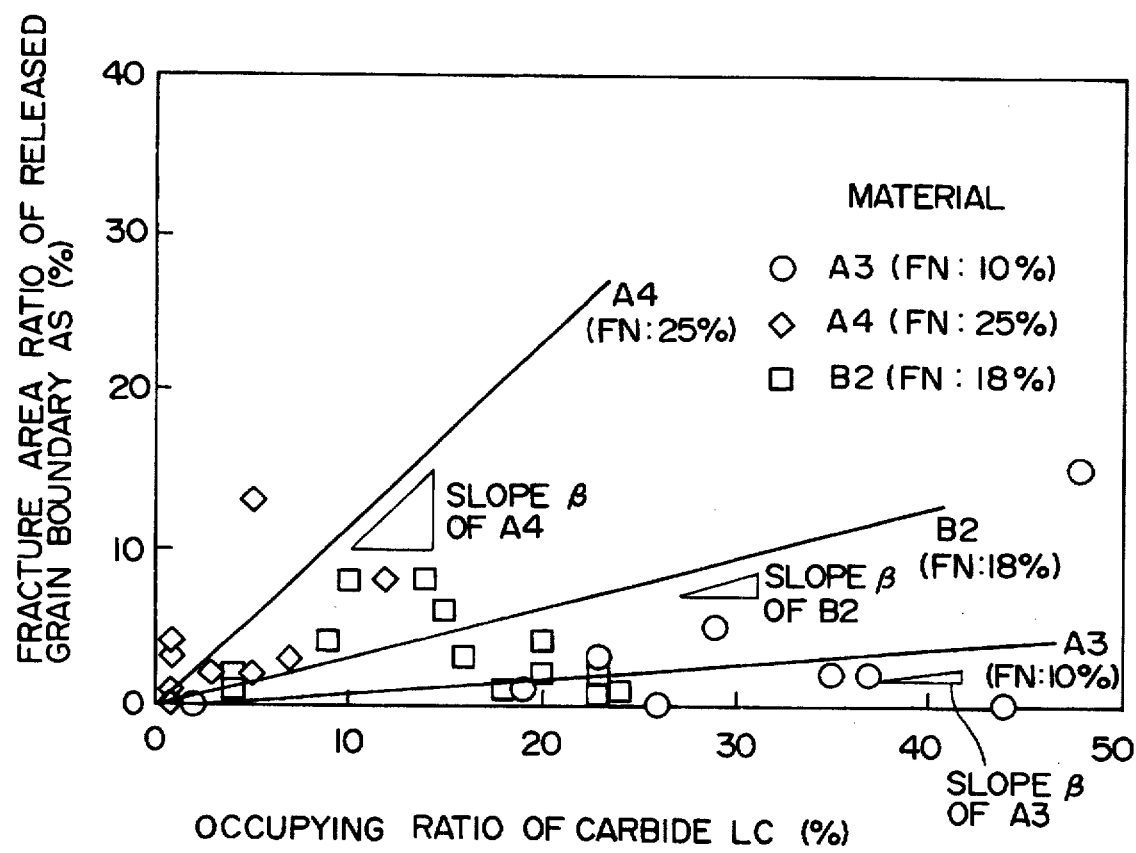
FIG. 12 is a characteristic drawing showing the relationship between the fracture ratio of released grain boundary (AS) and the occupying ratio of carbide (LC).
Figure 14:
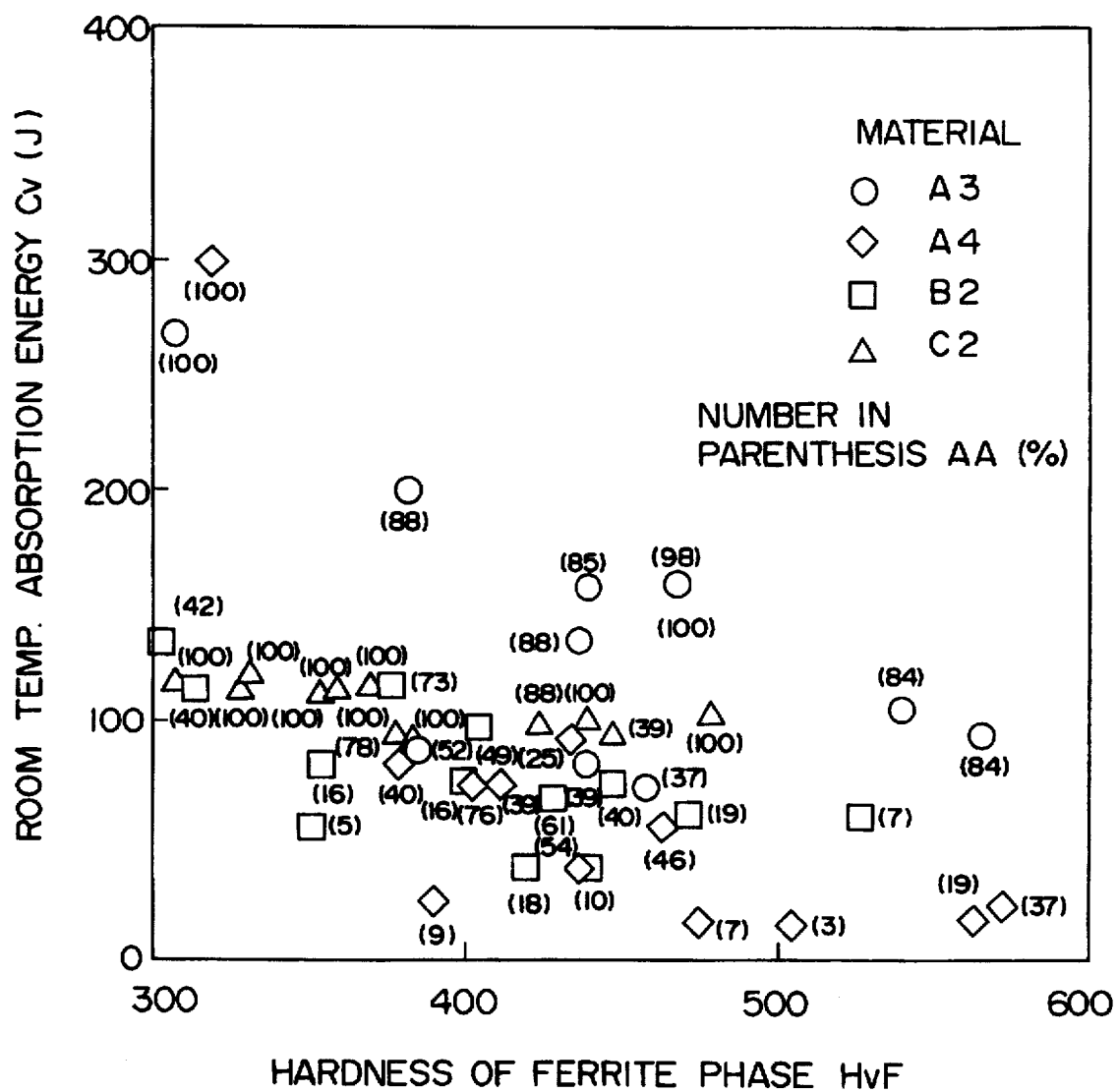
FIG. 14 is a characteristic drawing showing the relationship among experimentally determined impact absorption energy at room temperature, the hardness of the ferrite phase and the fracture ratio of the austenite phase.

FIG. 14 shows the relationship between Experimental $C_v$ and $H_vF$. As can be seen from FIG. 14, the Charpy absorption energy of each material tends to decrease with increasing hardness of the ferrite phase. FIG. 12 shows the relationship between the fracture ratio of released grain boundary (AS) and the occupying ratio of carbide (LC).

We claim:

1. A method of detecting an embrittlement of two-phase stainless steel, which comprises measuring the hardness of a ferrite phase, the hardness of an austenite phase of two-phase stainless steel, in conjunction with measuring an area ratio of the ferrite phase, a space between the ferrite phases, and an occupying ratio of carbide in the grain boundary length from microstructure observation to estimate a Charpy impact absorption energy at room temperature of the two-phase stainless steel from the above specified measurements.

* * * * *